United States Patent
Kotlik et al.

(10) Patent No.: US 7,221,980 B2
(45) Date of Patent: May 22, 2007

(54) ELECTROSTIMULATION SYSTEM WITH ELECTROMYOGRAPHIC AND VISUAL BIOFEEDBACK

(75) Inventors: Ben-Zion Kotlik, Shlomi (IL); Morris Zuker, Kiriat Bielk (IL)

(73) Assignee: Stimel Ltd., Naharya (IL)

( * ) Notice: Subject to any disclaimer, the term of this patent is extended or adjusted under 35 U.S.C. 154(b) by 600 days.

(21) Appl. No.: 10/344,598

(22) PCT Filed: Aug. 14, 2001

(86) PCT No.: PCT/IL01/00752

§ 371 (c)(1),
(2), (4) Date: Mar. 21, 2003

(87) PCT Pub. No.: WO02/13673

PCT Pub. Date: Feb. 21, 2002

(65) Prior Publication Data

US 2003/0208246 A1    Nov. 6, 2003

Related U.S. Application Data

(60) Provisional application No. 60/225,471, filed on Aug. 15, 2000.

(51) Int. Cl.
*A61N 1/18* (2006.01)

(52) U.S. Cl. ...................................................... 607/48

(58) Field of Classification Search ............... 607/48, 607/49; 600/546
See application file for complete search history.

(56) References Cited

U.S. PATENT DOCUMENTS 5,810,747 A * 9/1998 Brudny et al. .............. 600/595

* cited by examiner

*Primary Examiner*—Jeffrey R. Jastrzab
(74) *Attorney, Agent, or Firm*—Wolf, Block, Schorr & Solis-Cohen LLP; William H. Dippert

(57) ABSTRACT

The device of the present invention provided an electrostimulation system with electromyographic and visual biofeed back for sensing electromyographic impulses and facilitating muscular activity. The electrostimulation system comprises stimulator that is adapted to generate an electric impulse and at least one pair of electrodes adapted to transmit the electric impulse or to receive electromyographic impulses. The system further comprises an amplifier electrically communicating with the pair of electrodes, the amplifier is adapted to amplify the received electromyographic impulses and a filtering unit electrically communicating with the amplifier and is adapted to remove artifacts from the received electromyographic impulse. A commutation block is electrically communicating with the pair of electrodes and is adapted to alternately transfer the electromyographic impulses to the amplifier or to transfer the generated electric impulse from the stimulator. A display for displaying the received electromyographic impulses and a predetermined threshold value is also provided as well as a control unit that is adapted to receive the electromyographic impulses from the amplifier and to activate the stimulator in a predetermined manner. The stimulator incorporated in the present invention is triggered to transmit impulses to the rehabilitated muscle when the electromyographic impulse substantially equals or exceeds the predetermined threshold value.

16 Claims, 6 Drawing Sheets

ELECTROSTIMULATION SYSTEM WITH ELECTROMYOGRAPHIC AND VISUAL BIOFEEDBACK

CROSS REFERENCE TO RELATED APPLICATION

This application claims the benefit of the following dates of the U.S. Provisional Patent Application No. 60/225,471 filed on Aug. 15, 2000 and the International Application No. PCT/IL01/00752, filed Aug. 14, 2001, that designates the United States of America and which claims priority from U.S. Provisional Patent Application No. 60/225,471 filed on Aug. 15, 2000, each of which is incorporated herein by reference in its entirety.

FIELD OF THE INVENTION

The present invention relates to electrotherapy. More particularly, the present invention relates to a system for electrostimulation with electromyographic and visual feedback.

BACKGROUND OF THE INVENTION

Functional electrical stimulation (FES), in which stimulation of nerves is conducted, is a method known for several decades and has been used for activating paralyzed muscles. The conventional treatment methods of rehabilitation movement functions of post CVA patients are based on electrostimulation, while the patient plays a passive role in the process of therapy.

Electrical massage is known by the term TENS (transcutaneous electrical nerve stimulation). TENS acts as a pain reducer. The stimulation of the muscles causes a higher blood flow to the area, hence a massage effect. TENS causes also the release of endorphins for further ease of the pain.

Assisting the muscular contraction by affecting a muscle with a stimulating impulse is known and used. For example, an assisting apparatus is disclosed in U.S. Pat. No. 4,785,813 "Apparatus for Assisting Muscular Contraction" filed in 1986 by Petrofsky. This system is for assisting contraction of a partially paralyzed muscle. The system uses a pair of electrode terminals, which sense voluntary electromyogram (EMG) impulses at the site of the muscle and periodically transmit appropriately corresponding higher-level stimulation impulses.

One of the rehabilitation processes used for patients suffering from partial muscle paralysis such as CVA patients is the reeducation of the muscle to conduct voluntary actions. Another example that takes the above considerations into account is U.S. Pat. No. 4,811,742 "Proportional Response Electrical Muscle Stimulation" filed in 1985 by Hassel et al. This patent discloses measuring the excitation of the skeletal musculature of a subject by an EMG, processing it and controllably applying to the musculature EMG impulses that are proportional to the electrical nerve impulses. This invention is useful for reeducation and/or amplification of muscular control.

The display of the EMG impulses for the selection of transmitted impulses is also a known prior art. Such a device was filed in 1992 and is disclosed in U.S. Pat. No. 5,300,096 "Electromyographic Treatment Device" by Hall et al. This invention discloses an electrical muscle stimulator that converts EMG impulses to digital words for the analysis and display by a computer program. The therapists selects a variety of different parameters appropriate for the individual patient, and instruct the device to initiate stimulating impulses on command, or upon detection of a suitable EMG impulse from the patient. The device can digitally model a wide variety of waveforms and graphically assist the therapist in developing and shaping various wave pulse trains.

Control over the process of muscles rehabilitation may be achieved upon the combination of transmitting impulses to the muscle similarly to the methods indicated herein above with receiving some indication from the muscle on its function or response. Such combination is disclosed in U.S. Pat. No. 5,549,656 "Combination Neuromuscular Stimulator and Electromyograph System" filed in 1995 by Reiss. This patent discloses a combined dual channel electromuscular stimulator for directing electrical pulses into the skin and a dual electromyography for detecting electrical impulses generated in muscles. Another example for a controlled system was filed in 1987 and is disclosed by Barry et al. in U.S. Pat. No. 4,805,636 "System for Controlling Muscle Response". This system for controlling muscular responses in living beings utilizes electrical stimulation of the muscle and acoustic monitoring of muscle performance. In one aspect, muscle functioning during a physical activity can be monitored acoustically, and the resulting impulse compared against predetermined impulse characteristics. Deviation of the muscle function from the desired characteristic can be corrected by applying a responsive electrical impulse.

In all former disclosed devices and methods, including the controlled devices, the methods focus on the therapist abilities to transmit impulses to the patient or to receive information. The patient in all the previous methods is a passive being that is activated by transmission of electrical stimulation. The patient is not contributing to his rehabilitation and has no control over his treatment. In rehabilitation processes in general, and also in many other therapeutic treatments, the collaboration and motivation of the patient in the process is very important to its success. The activation of muscles is a voluntary action in which the contribution of activating and participating the patient to the success of the process is evident.

SUMMARY OF THE INVENTION

It is an object of the present invention to provide an electrostimulation system that enables the patient to serve as an active being and participate in the treatment process by his voluntary will.

It is an additional object of the present invention to provide an electrostimulation system provided with a pair of skin surface electrodes and a reference electrode. The same pair of skin surface electrodes is used for measuring EMG impulses and for providing stimulating currents. By using the same pair of electrodes, the muscle that transmits the EMG impulse is the same muscle that is being stimulated.

Yet, it is another object of the present invention to provide an electrostimulation system that produces and transmits impulses that facilitate restoring the natural movements of the muscles.

It is another object of the present invention to provide an electrostimulation system provided with a display that visualizes the level of EMG impulses produced by the patient.

It is yet another object of the present invention to provide an electrostimulation system in which the therapist feeds the system with predetermined target values to which the patient may reach using his voluntary will. After the patient reaches the target values, the electrostimulation system transmits corresponding stimulation pulses to the patient, in an educational manner.

Additionally, it is an object of the present invention to provide an electrostimulation system provided with the possibility to set the amplitude of a stimulation impulse in conventional stimulation therapy equipment that uses absolute units (milliamperes). The improved system will use threshold units from the EMG measurement for setting the amplitude of the stimulation impulse. Accordingly, the new system permits gradual muscle contraction in a wide range of amplitudes.

It is thus provided an electrostimulation system with electromyographic and visual biofeedback for sensing electromyographic impulses and facilitating muscular activity, said electrostimulation system comprising:
- stimulator adapted to generate an electric impulse;
- at least one pair of electrodes adapted to transmit said electric impulse or to receive electromyographic impulses;
- amplifier electrically communicating with said at least one pair of electrodes, said amplifier adapted to amplify said received electromyographic impulses;
- filtering unit electrically communicating with said amplifier, said filtering unit is adapted to remove artifacts from the received electromyographic impulse;
- commutation block electrically communicating with said at least one pair of electrodes, said commutation block adapted to alternately transfer the electromyographic impulses to said amplifier or to transfer the generated electric impulse from said stimulator;
- display for displaying said received electromyographic impulses and a predetermined threshold value;
- a control unit adapted to receive the electromyographic impulses from said amplifier and to activate said stimulator in a predetermined manner;
- wherein said stimulator is triggered to transmit the electric impulse when the electromyographic impulse substantially equals or exceeds the predetermined threshold value.

Furthermore, in accordance with another preferred embodiment of the present invention, a reference electrode is electrically communicating with said amplifier.

Furthermore, in accordance with another preferred embodiment of the present invention, an integrator is electrically communicating with said filtering unit, said integrator is adapted to smooth and recondition the electromyographic impulse that is received from said filtering unit so that the impulse may be displayed on said display.

Furthermore, in accordance with another preferred embodiment of the present invention, an additional amplifier is electrically communicating with said integrator and with said display so that the electromyographic impulse outgoing from said integrator to said display is further amplified.

Furthermore, in accordance with another preferred embodiment of the present invention, said predetermined threshold value is manually fed to said display by a trigger setting.

Furthermore, in accordance with another preferred embodiment of the present invention, a comparator is electrically communicating with said trigger setting as well as with said amplifier.

Furthermore, in accordance with another preferred embodiment of the present invention, said comparator is adapted to change a mode of said commutation block from transferring the electromyographic impulses to said amplifier to transferring the generated electric impulse from said stimulator when the electromyographic impulse reaches said predetermined threshold value.

Furthermore, in accordance with another preferred embodiment of the present invention, a remote control unit is communicating with said control unit.

Furthermore, in accordance with another preferred embodiment of the present invention, said display is a linear graphic bar display.

Furthermore, in accordance with another preferred embodiment of the present invention, said stimulator comprises:
- pulse modulator adapted to construct said electric impulse;
- amplitude modulator adapted to set the amplitude of said electric impulse;
- CPU unit electrically communicating with said pulse modulator;
- Control unit electrically communicating with said CPU unit, said control unit adapted to determine parameters of the pulse modulator and the amplitude modulator;
- setting unit adapted to determine a threshold value and a maximum value of said electric impulse;
- output block electrically communicating with said CPU unit, with said pulse modulator and with said setting unit, said output block transfers the electrical impulse to said commutation block and/or to said at least one pair of electrodes.

Furthermore, in accordance with another preferred embodiment of the present invention, said stimulator further comprises a display, said display is electrically communicating with said CPU unit.

Furthermore, in accordance with another preferred embodiment of the present invention, said setting unit comprises current setting and threshold setting, said current setting is adapted to perform a current adjustment, said threshold setting is adapted to prevent pain during muscular activity by setting a threshold value.

Furthermore, in accordance with another preferred embodiment of the present invention, said setting unit is electrically communicating with a summing amplifier, said summing amplifier amplifies the electrical impulse and transfers it to said output block.

It is thus further provided a method for stimulating muscles that are in a rehabilitation process of a patient, said method comprising:
- providing an electrostimulation system with electromyographic and visual biofeedback that comprises
  - a stimulator adapted to generate an electric impulse;
  - at least one pair of electrodes adapted to transmit said electric impulse or to receive electromyographic impulses;
  - amplifier electrically communicating with said at least one pair of electrodes, said amplifier adapted to amplify said received electromyographic impulses;
  - filtering unit electrically communicating with said amplifier, said filtering unit is adapted to remove artifacts from the received electromyographic impulse.
  - commutation block electrically communicating with said at least one pair of electrodes, said commutation block adapted to alternately transfer the electromyographic impulses to said amplifier or to transfer the generated electric impulse from said stimulator;
  - display for displaying said received electromyographic impulses and a predetermined threshold value;

a control unit adapted to receive the electromyographic impulses from said amplifier and to activate said stimulator in a predetermined manner;

adhering said a least one pair of electrodes to the rehabilitated muscles;

providing a reference electrode;

adhering said reference electrode to the patient in a location relatively remote from the rehabilitated muscles;

connecting said reference electrode to said amplifier;

transmit said electric impulse to the muscles through said at least one pair of electrodes.

Furthermore, in accordance with another preferred embodiment of the present invention, the method further comprises:

receiving electromyographic impulses;

feeding said predetermined threshold value;

comparing said electromyographic impulses to said predetermined threshold value;

transmitting an electric impulse having higher amplitude than the amplitude of the received electromyographic impulse having the highest value to the muscles after said electromyographic impulse exceeds said predetermined threshold value.

And additionally, in another embodiment of the present invention, the method further comprises displaying the transmitted electric impulse on said display and displaying said predetermined threshold value.

DETAILED DESCRIPTION OF THE INVENTION AND FIGURES

The present invention provides new and unique apparatus and method for the treatment of patient suffering from partial paralysis such as in cases of post CVA. In those cases and in others, the connection between the nerves and the muscles; hence transfer of information to the muscles, is damaged. In order to reeducate the muscular system to voluntary activate the muscles, impulses from another source have to be transmitted to the muscles. The present invention provides an electrostimulation system that produces and transmits impulses to the patient's muscles that facilitate restoring the natural movements of the muscles. Alternately, the system receives EMG voluntary impulses from the patient so that a biofeedback is received. The biofeedback system facilitates the patient to comprehend and distinct between his own will to move the muscle and the actual movements of the muscle.

Figure 1:
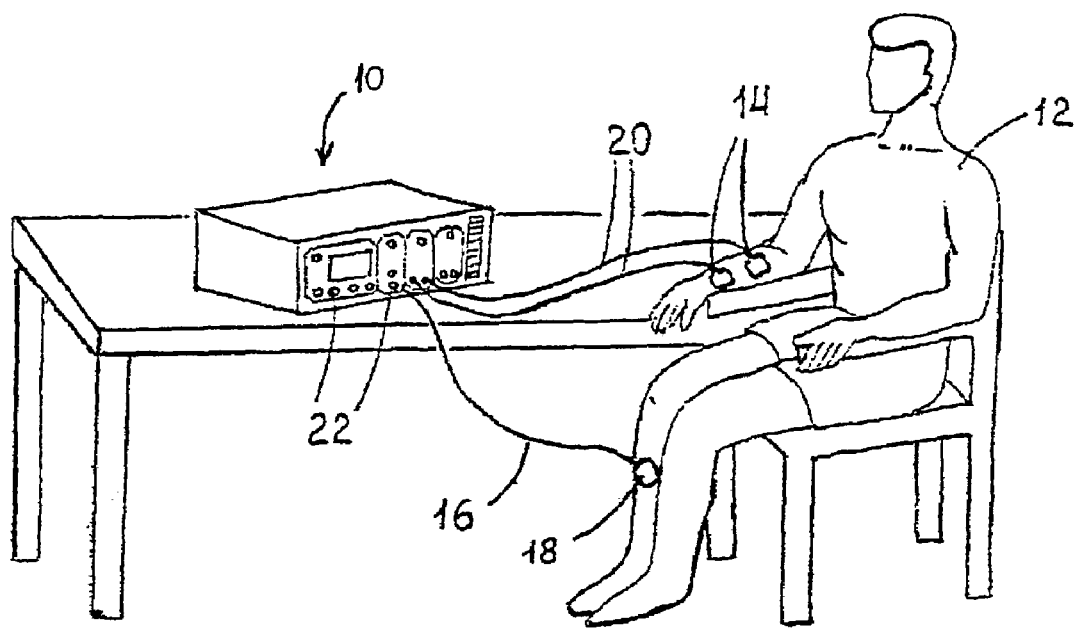
FIG. 1 illustrates an electrostimulation system with electromyographic and visual biofeedback in accordance with a preferred embodiment of the present invention, attached to a patient through skin electrodes.

Reference is now made to FIG. 1 illustrating an electrostimulation system with electromyographic and visual biofeedback in accordance with a preferred embodiment of the present invention, attached to a patient through skin electrodes. A dual channel Electrostimulation system with biofeedback 10 may function in three possible modes:

1. Stimulation mode: An electrostimulation system generates specially modulated bipolar currents in two channels simultaneously or intermittently. The electrostimulation system then transmits the stimulating impulses to the patient's muscles through skin surface electrodes according to the needs of the specific patient. The patient receives an impulse that is preferably a train (series) of specially modulated current impulses. Impulse parameters such as duration, repetition rate, maximal amplitude and threshold point can be determined by a therapist.

2. Remote control stimulation mode: similarly to the stimulation mode, however one series of stimulation currents is transmitted and the operation may be remotely activated. In this mode, the patient as well as a therapist may operate the stimulation system upon their will.

3. Biofeedback stimulation mode: operation according to a mode of receiving/transmitting of impulses. An electrostimulation system receives EMG impulses from a patient that voluntarily and gradually tries to activate the muscle according to his own efforts. At a certain predetermined threshold value, the electrostimulation system is triggered to transmit impulses to the muscle. The transmitted impulse has higher values than the received ones. This is a re-educational mode.

Electrostimulation system with biofeedback 10 transmits impulses to a patient 12 through to pair of skin surface electrodes 14. Skin surface electrodes 14 are electrically connected to the device by electric wires 20. Surface electrodes 14 are adhered to patient 12 at a location close to the stimulated muscle that is in a rehabilitation process. Reference electrode 18 is electrically connected to the device by electric wire 16 and is adhered to patient 12 in a location that is relatively remote from the location where skin electrodes 14 are adhered. Electrostimulation system with biofeedback 10 is provided with panels of knobs 22 through which instructions are given to a control unit as will be comprehensively explained herein after.

Figure 2:
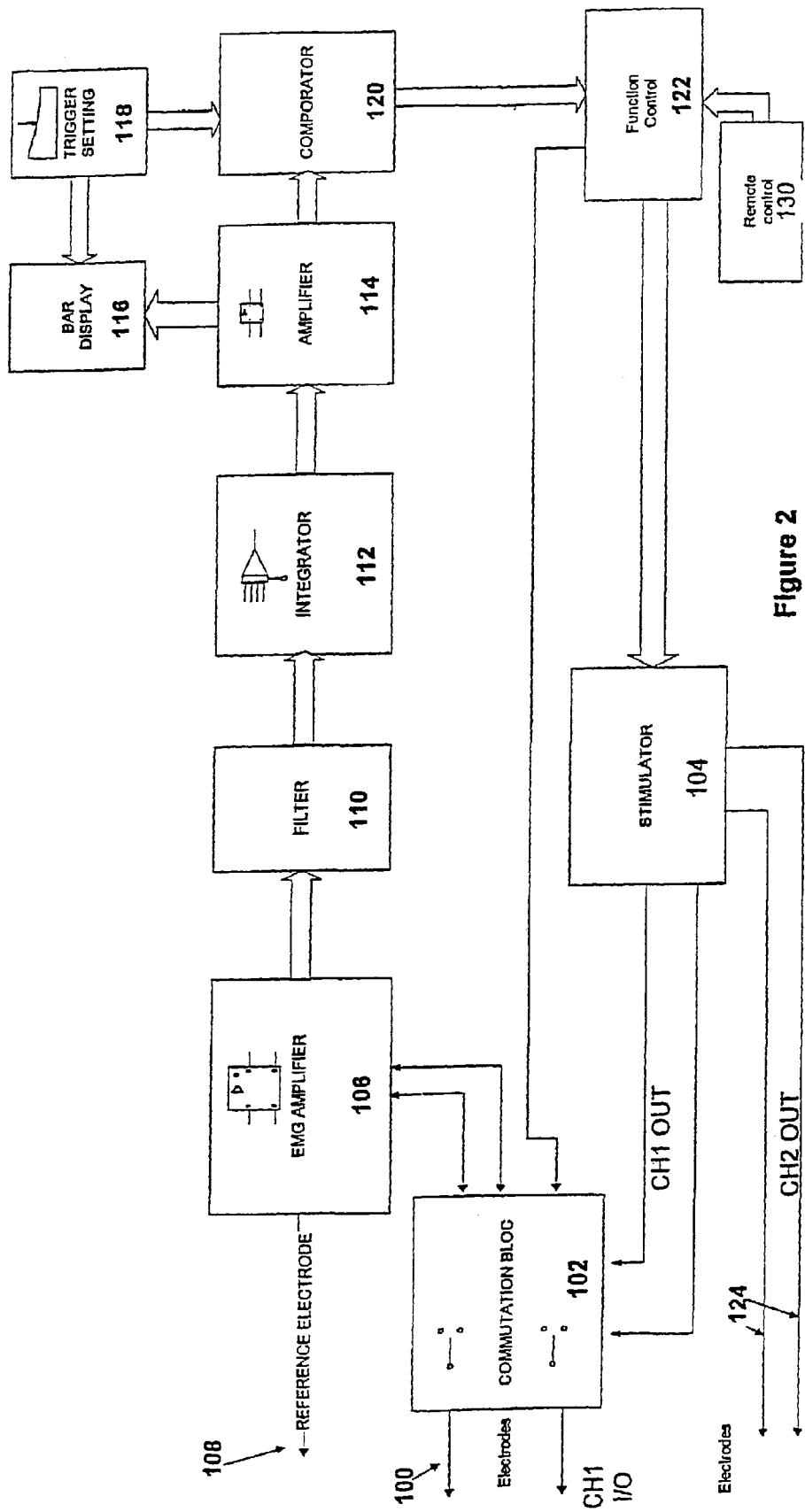
FIG. 2 illustrates a block diagram of an electrostimulation system with electromyographic and visual biofeedback in accordance with a preferred embodiment of the present invention.

Reference is now made to FIG. 2 illustrating a block diagram of an electrostimulation system with electromyographic and visual biofeedback in accordance with a preferred embodiment of the present invention. Pair of electrodes 100, which is connected to a patient (shown in FIG. 1), is electrically communicating with a commutation block 102. Pair of electrodes 100 is referred to as CH1 (channel 1) and may receive current as well as transmit. Commutation block 102 transfers currents that are received through electrodes 100 from the patient or currents transmitted through the electrodes from a stimulator 104 to the patient. Stimulator 104 is an electronic generator of impulses. A comprehensive description of a stimulator in accordance with a preferred embodiment of the present invention will be given herein after. An impulse that is received from the patient is transferred to an electromyographic (EMG) amplifier 106. EMG amplifier 106 is electrically communicating with the patient through an additional electrode, a reference electrode 108. The difference between both electrodes designated as CH1 in respect with reference electrode 108 is the impulse that is measured. The measured impulse represents the signal that is sent by the brain to the muscle in order to activate it. Reference electrode prevents artifacts generated by the body of the patient or by external electric field.

As indicated herein before, the patient is suffering from lack or defected communication between the currents from the brain and the muscles; hence the muscle does not receive the impulse or receives a weakened impulse that produces a weakened action. This impulse is to be amplified by EMG amplifier 106. The amplified impulse is then transferred through filter 110 in order to reduce disturbances and other artifacts. Filter 110 filters out residual electrical activity and furthers on the impulse that is delivered to the muscle by the brain. Possible artifacts from the main electricity system are also removed in this stage. The resulting filtered impulse enters an integrator 112 that integrate the impulse to a dc voltage level that is proportional to the muscle contraction. Integrator 112 is adapted to smooth the impulse and recondition it for visual display and observation. The resulted impulse is then amplified in amplifier 114 to values in which suffice resolution is attained and displayed on display 116. Display 116 is preferably a linear graphic bar display.

The therapist and the patient can see on display 116 the actual voluntary efforts of the patient to produce an action in a specific muscle in order to move a certain organ. The patient becomes involved in the rehabilitation process since he may observe his evolving efforts to move an organ. Display 116 displays also a threshold value that indicates a certain predetermined value to which the patient should be motivated to reach. Since the patient may see on display 116 the result of his real efforts to move an organ and the value to which he should reach, he is totally participating in the rehabilitation process and may be fully motivated and committed to its success. The threshold value may be varied according to the will, the advancement, the ability and the state of a specific patient by the therapist. The threshold value is fed to display 116 from trigger setting 118, which transfers this value also to a comparator 120.

Comporator 120 receives information from two sources: the threshold value from trigger setting 118 and values from amplifier 114 indicating the actual activity of the muscle. Comporator 120 is adapted to instruct commutation block 102 to change the mode of action from muscle impulse receiving to stimulating impulse transmitting when the values transferred from amplifier 114 reach the threshold value in trigger setting 118. The patient, after making a successful effort to reach a predetermined impulse value, is stimulated by a certain current that establishes a reaction or movement of an organ that is compatible to his effort. This is an important step in the reeducation process that accompanied the rehabilitation process. The patient, instead of receiving unexpected impulses that produces action of the muscle without any possibility to evaluate the effort of the patient in order to produce such as action on his own, receive an indicated impulse as a reword for his efforts. Comporator 120 transfers the instruction for stimulating through function control block 122. After stimulation is accomplished, commutation block 102 switched back to a receiving mode, in which detection of muscular activity is performed.

Selecting the mode of operation is accomplished using function control block 122. The selection is between three modes that were referred to herein before:
1. stimulation mode;
2. remote control stimulation mode;
3. biofeedback stimulation mode.

In the stimulation modes, the branch of receiving EMG impulses is eliminated and the visual biofeedback is abandoned. Commutation block 102 transfers stimulation impulses through CH1 only from stimulator 104 or, on the other hand, impulses may be transferred from stimulator 104 through another pair of electrodes 124, referred herein as CH2. A remote control unit 130 may transfer instruction to function control block 122 so as to activate the remote control possibility.

Figure 3:
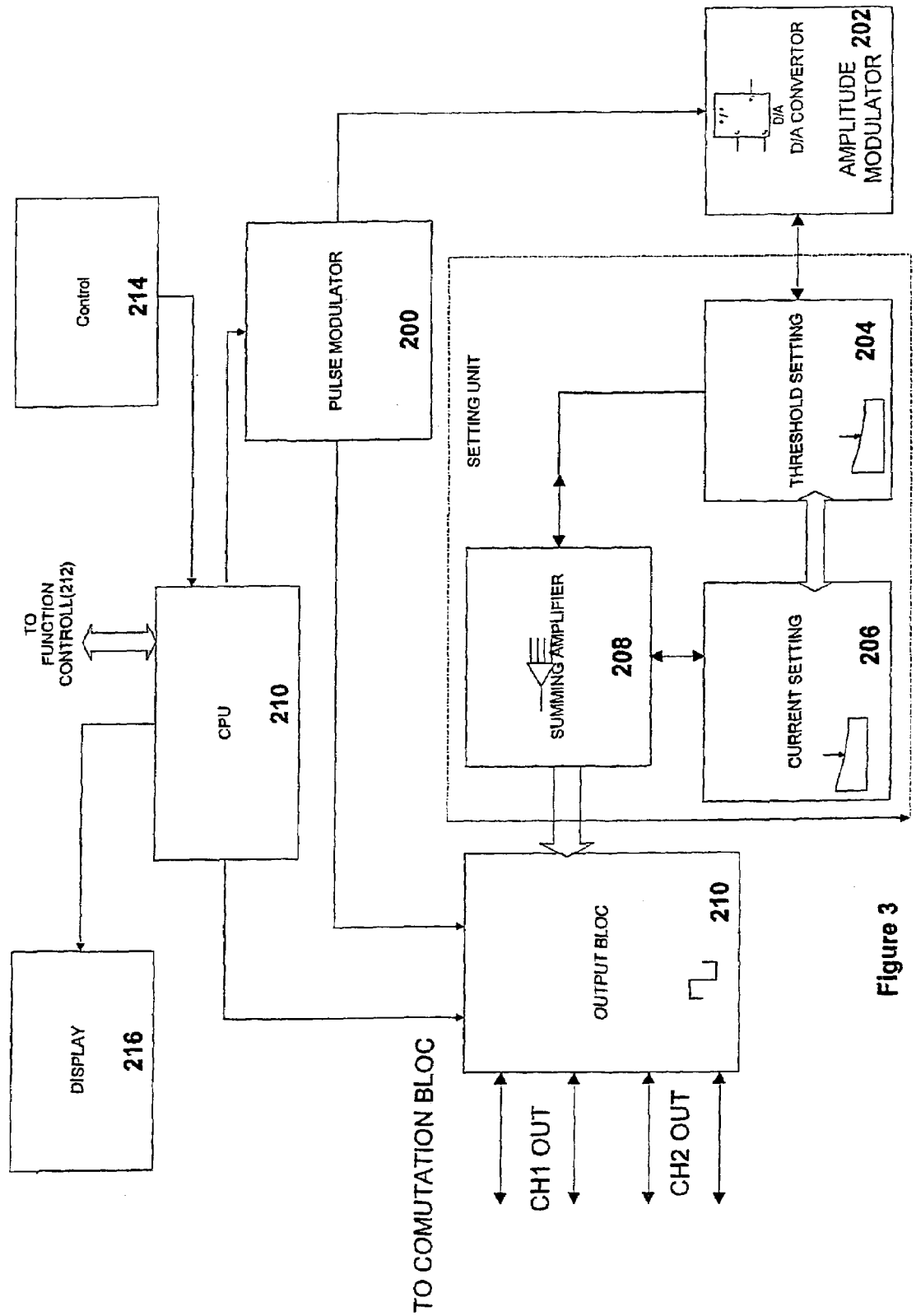
FIG. 3 illustrates a block diagram of the stimulator unit shown in FIG. 2.

Reference is now made to FIG. 3 illustrating a block diagram of the stimulator shown in FIG. 2. Stimulator 104 is adapted to generate impulses that are characterized in stimulating the muscle or the nerves so as to spread excitations and cause an action of an organ without causing pain or discomfort. The stimulator comprises a pulse modulator 200 that constructs a series of impulses. The modulator is constructed so that it maintains a certain form and shape of an impulse. The shape of the impulse of the present invention is constructed in a way so that a "natural action" by the activated organ is originated. The term natural action by an organ is referred to an action that is relatively smooth and not sudden as well as an action that is not twisted into directions that are not usually performed by healthy subjects. Patients experimentally treated by the stimulator of the present invention report that the stimulation is relatively delicate and it lessens significantly the natural fear patients feel in such treatments. This also enhances the motivation of patients towards the stimulation treatments.

Figure 4:
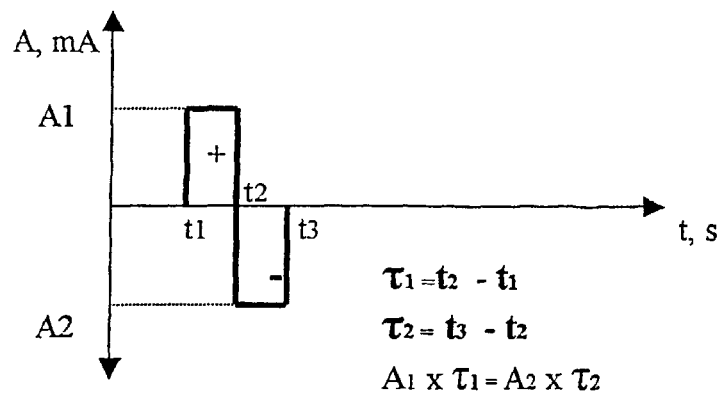
FIG. 4 illustrates a usual rectangular impulse that may be used in the electrostimulation system with electromyographic and visual biofeedback of the present invention.

The most widely used impulses that are used in neuromuscular stimulation are electric current impulses. The most effective form of electric impulse is a rectangular form. Reference is now made to FIG. 4 illustrating a usual rectangular impulse that may be used in the electrostimulation system with electromyographic and visual biofeedback of the present invention. Bipolar impulses are used in order to prevent polarization of the electrodes; thus the quantity of electricity (defined as the current multiplied by duration of the impulse) that is used in the negative and the positive parts of the impulse should be almost equal. As a result of an impulse shown in FIG. 4, the spreading excitation in the muscle may start before the end of the first impulse (the positive part), depending on the duration of the impulse. As a result, when the second part of the impulse having the inverse polarity is being transferred, there will be no response to it.

Figure 5:
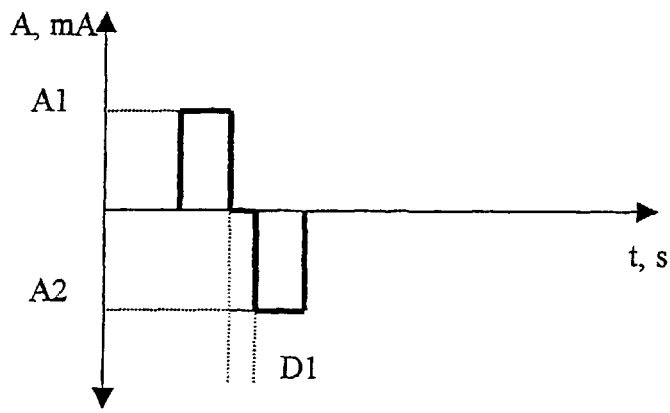
FIG. 5 illustrates a usual rectangular impulse with a delay that may be preferably used in the electrostimulation system with electromyographic and visual biofeedback of the present invention.

Reference is now made to FIG. 5, illustrating a usual rectangular impulse with a delay. The muscles are excited from the impulse through nerve fibers. Only a part of the fibers won't be excited from the impulse since they have a higher threshold. During the first positive part of the impulse, changes in the membrane potential of this nerve's fibers will not reach the threshold and as a consequence, will not cause a spreading excitation. However, some of these nerve fibers, for which the influence of the impulse is relatively close to their threshold, generate local active potential. While those local potentials are developing, they can reach the threshold and cause a spreading action potential even though the first part of the impulse had already ended. It is desirable that the second impulse part, which has an inverse polarity, will not inhibit the local active potential from reaching the threshold and cause the increase in the quantity of excited fibers. For that reason, the second part should be delayed. The delay of the second inverse part of the impulse should be about 0.12 ms after the end of the first part of the impulse.

Figure 6:
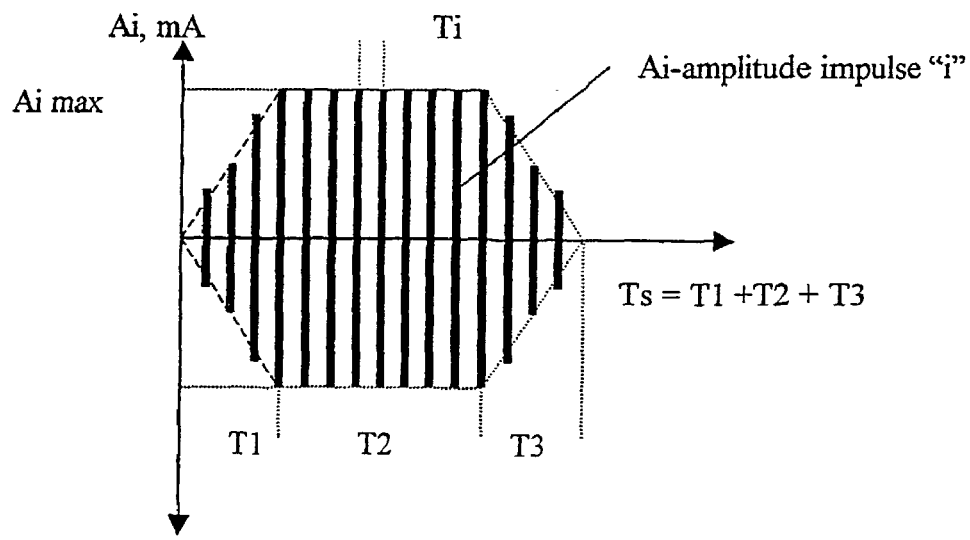
FIG. 6 illustrates amplitude modulation in accordance with a preferred embodiment of the present invention.

Reference is now made to FIG. 6 illustrating amplitude modulation in accordance with a preferred embodiment of the present invention. Generally, the impulse sequence should be modulated in order to reach an adequate contraction dynamics of the stimulated muscle. The quantity of excited motor units is changed in accordance with impulse amplitude and is determined by amplitude modulation. Smooth dynamics of the invoked muscle contraction can be reached by choosing the appropriate parameters of the modulation in order to establish a contraction that is similar to the voluntary contraction. An example for parameters that adequate a smooth contraction in accordance with a preferred embodiment of the present invention is as follows:

$A_1 \max \leq 75$ mA $T_1 = T_2 = 0.25$ Ts $T_3 = 0.5$ Ts

Figure 7:
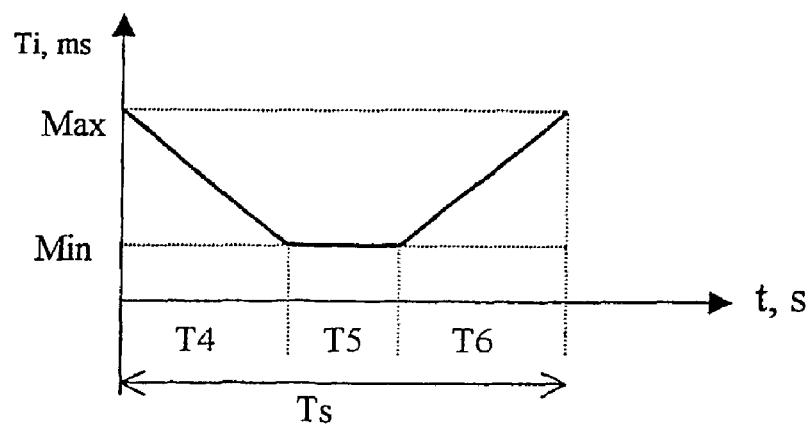
FIG. 7 illustrates frequency modulation in accordance with a preferred embodiment of the present invention.

Reference is now made to FIG. 7 illustrating frequency modulation in accordance with a preferred embodiment of the present invention. A decrease in the period of impulse repetition increases the strength of contraction of the excited motor unit. An example for parameters that adequate a smooth contraction in accordance with a preferred embodiment of the present invention is as follows:

$T_i \max = 70$ mS $T_i \min = 23$ mS $T_4 = T_6 = \frac{3}{8}$ Ts $T_5 = \frac{2}{6}$ Ts During amplitude modulation, the duration of the invoked muscle contraction Tm is always less than the duration of the impulse sequence Ts because of the excitation threshold. There is a discrepancy between the desired contraction duration, Ts, and the contraction duration obtained, Tm. In order to eliminate this discrepancy, impulse amplitude modulation should start from a threshold level referred to as $A_{io}$ instead of zero level.

Usually, there is a large dispersion of individual threshold values. It is possible that the physiotherapist will set the starting level of the impulse amplitude above the threshold level or even above the level that causes the maximal response of the muscle. As a result, the patient may feel discomfort or even pain and his motivation to receive the electrostimulation treatment decreases. The decrease in the motivation of the patient influences directly the effectiveness of the treatment. This problem usually arises when the amplitude of the stimulating impulses is regulated using a single scale with absolute units (mA or V). In order to avoid this problem, the method and device of the present invention suggests setting and adjusting the amplitude of the stimulating impulses using two regulators: a threshold regulator and multiplier regulator. The threshold regulator changes the amplitude of stimulation impulses in the range of low amplitudes (for example from 0 to 25 mA) in order to set the amplitude of impulses equal to individual threshold value for sensitivity. The multiplier regulator for setting a strength of muscle contraction is set by the multiplier in the range from 1 to 3 relative threshold units. Using a large range of impulses with amplitude of 4.5 threshold units will probably cause painful irritation.

Figure 8:
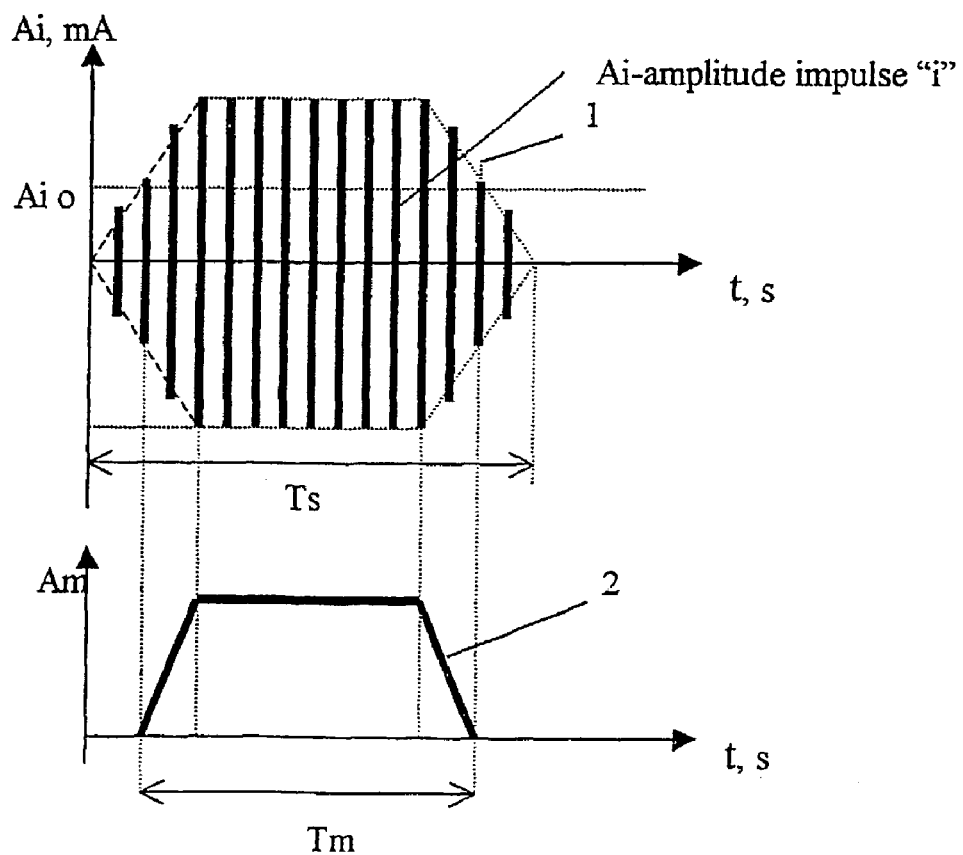
FIG. 8 illustrates duration of muscle contraction in accordance with a preferred embodiment of the present invention.
Figure 9:
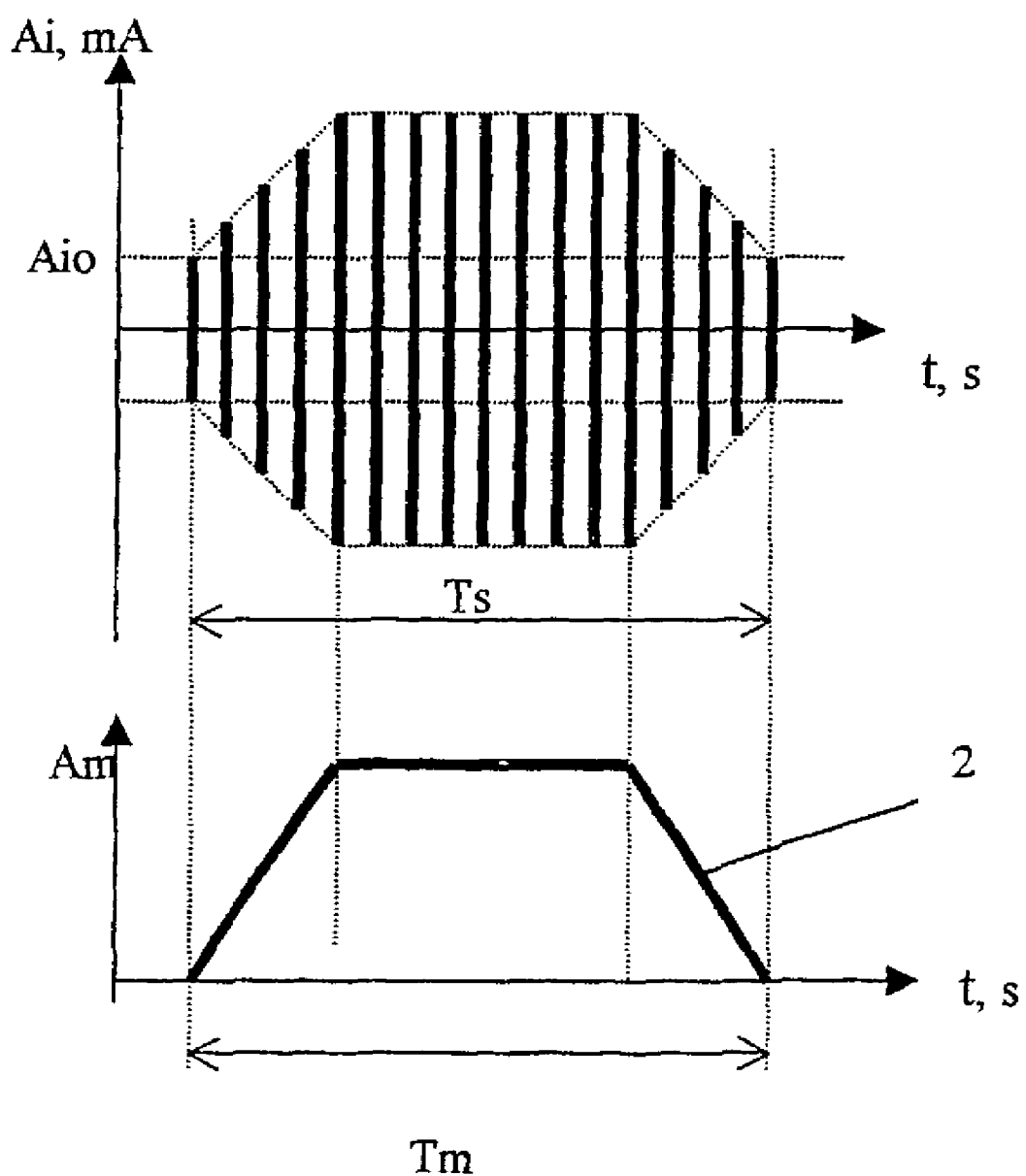
FIG. 9 illustrates duration of muscle contraction and use of threshold amplitude in accordance with another preferred embodiment of the present invention.

Reference is now made to FIGS. 8 and 9 illustrating duration of muscle contraction in accordance with preferred embodiments of the present invention. Both figures depict the bounding curve of the amplitude of bipolar impulses and the muscle contraction dynamics. Curve that is marked with the number 1 is the bounding curve of the amplitude of bipolar impulses and the curve marked with the number 2 is the bounding curve of the amplitude of muscle contraction. Iio is the threshold impulses amplitude and Am, Tm are the amplitude and duration of muscle contraction, respectively.

Returning to FIG. 3, pulse modulator 200 transfers the information regarding the type of pulse and its shape to an amplitude modulator 202 that acts as a D/A converter. The generated impulse built in accordance to the preferred sequence shown herein before from both modulators, pulse modulator 200 and amplitude modulator 202, interacts with a setting cycle that accords the impulse to a specific patient. The parameters, $A_{io}$max, Ts and Tp/Ts are predetermined by the therapist that follows a certain program built for a certain patient. The program is usually built according to parameters such as the disabilities of the patient or his progress. The system and method of the present invention takes into account the variation in sensitivity of different patients towards the given impulse. A certain impulse having certain intensity provokes a different reaction from different patients. An impulse having a specific intensity may provoke an efficient reaction from one patient while for another patient, the same impulse provoke a feeling of pain. The system of the present invention enables a therapist to receive and use information from the stimulated organ in order to produce and transmit a stimulation impulse that correspond to the sensitivity of the patient and requires movement volume from the stimulated limb.

Amplitude modulator 202 interacts with a threshold setting 204 that adjusts the impulse to the sensitivity of the patient. For example, children have relatively high sensitivity; therefore, a pulse having relatively low intensity is required in order to stimulate their muscles. On the other hand, a subject having CVA has a low sensitivity and in this case, in order to achieve a reaction, a pulse having relatively high intensity is required. The sensitivity threshold is between 0-25 mA while the therapist tunes the intensity of the impulse to a degree in which the patient feels a certain excitation or twitches. Threshold setting 204 interacts with a current setting 206 in which the final adjustment of the current is encountered, $A_{imax}$. The current setting $A_{imax}$ may be tuned in block 206 from 1-3 (multipliers).

A summing amplifier 208 sums up the values from threshold setting 204 and current setting 206 so that the final pulse characteristics are constructed. The final build-up of the stimulation pulse is performed in an output block 210 that receives information on some characteristics of the pulse from block CPU 212, pulse modulator 200 and summing amplifier 208. Output block 210 provides current via surface electrodes 100 in the range of 0.1-75 mA. The frequency of the current in series of pulses may be modulated in the range between 30 Hz and 80 Hz. Output block 210 and pulse modulator 200 are electrically communicating with a CPU unit 212. Output block 210 transfers the resulting output pulses to surface electrodes 100 of CH1 via commutation block 102 (shown in FIG. 2) directly through CH2.

CPU unit 212 receives predetermined parameters of stimulation from a controller block 214. The processor is also electrically communicating with a display 216 on which the type and shape of the constructed pulse may be displayed as well as other information regarding the treatment.

The electrostimulation system with electromyographic and visual biofeedback carries precaution measures by currying out a self-test before the treatment begins and provides automatic emergency shutdown, in case of fault conditions.

The electrostimulation system with electromyographic and visual biofeedback is preferably powered by internal Nickel Metal rechargeable battery.

It should be clear that the description of the embodiments and attached Figures set forth in this specification serves only for a better understanding of the invention, without limiting its scope as covered by the following claims.

It should also be clear that a person skilled in the art, after reading the present specification could make adjustments or amendments to the attached Figures and above described embodiments that would still be covered by the following claims.

The invention claimed is:

1. An electrostimulation system with electromyographic and visual biofeedback for sensing electromyographic impulses and facilitating muscular activity, said electrostimulation system comprising:
    a stimulator adapted to generate an electric impulse;
    at least one pair of electrodes adapted to transmit said electric impulse or to receive electromyographic impulses;
    an amplifier electrically communicating with said at least one pair of electrodes, said amplifier adapted to amplify received electromyographic impulses;
    a filtering unit electrically communicating with said amplifier, said filtering unit being adapted to remove artifacts from the received electromyographic impulses;
    a commutation block electrically communicating with said at least one pair of electrodes, said commutation block being adapted to alternately transfer the received electromyographic impulses to said amplifier or to transfer the generated electric impulse from said stimulator;
    a display for displaying said received electromyographic impulses and a predetermined threshold value; and
    a control unit adapted to receive the amplified electromyographic impulses from said amplifier and to activate said stimulator in a predetermined manner,
    wherein said stimulator is triggered to transmit the electric impulse when the received electromyographic impulses substantially equal or exceed the predetermined threshold value.

2. The electrostimulation system as claimed in claim 1, wherein a reference electrode is electrically communicating with said amplifier.

3. The electrostimulation system a claimed in claim 1, wherein an integrator is electrically communicating with said filtering unit, said integrator is adapted to smooth and recondition the received electromyographic impulses that is received from said filtering unit so that the received electromyographic impulses may be displayed on said display.

4. The electrostimulation system as claimed in claim 3, wherein an additional amplifier is electrically communicating with said integrator and with said display so that the received electromyographic impulse impulses outgoing from said integrator to said display is further amplified.

5. The electrostimulation system as claimed in claim 1, wherein a trigger setting is provided for manually feeding said predetermined threshold value to said display.

6. The electrostimulation system as claimed in claim 5, wherein a comparator is electrically communicating with said trigger setting as well as with said amplifier.

7. The electrostimulation system as claimed in claim 6, wherein said comparator is adapted to change a mode of said commutation block from transferring the received electromyographic impulses to said amplifier to transferring the generated electric impulse from said stimulator when the received electromyographic impulse reaches said predetermined threshold value.

8. The electrostimulation system as claimed in claim 1, wherein a remote control unit is communicating with said control unit.

9. The electrostimulation system as claimed in claim 1, wherein said display is a linear graphic bar display.

10. The electrostimulation system as claimed in claim 1, wherein said stimulator comprises: a pulse modulator adapted to construct said electric impulse; an amplitude modulator adapted to set amplitude of said electric impulse; a CPU unit electrically communicating with said pulse modulator a control unit electrically communicating with said CPU unit, said control unit adapted to determine parameters of the pulse modulator and the amplitude modulator; a setting unit adapted to determine a threshold value and a maximum value of said electric impulse; an output block electrically communicating with said CPU unit, with said pulse modulator and with said setting unit, said output block transfers the electrical impulse to said commutation block and/or to said at least one pair of electrodes.

11. The electrostimulation system as claimed in claim 10, wherein said stimulator further comprises a display, said display is electrically communicating with said CPU unit.

12. The electrostimulation system as claimed in claim 10, wherein said setting unit comprises current setting and threshold setting, said current setting is adapted to perform a current adjustment, said threshold setting is adapted to prevent pain during muscular activity by setting a threshold value.

13. The electrostimulation system as claimed in claim 10, wherein said setting unit is electrically communicating with a summing amplifier, said summing amplifier amplifies the electrical impulse and transfers it to said output block.

14. A method for stimulating muscles that are in a rehabilitation process of a patient, said method comprising:
    providing an electrostimulation system with electromyographic and visual biofeedback that comprises a stimulator adapted to generate an electric impulse; at least one pair of electrodes adapted to transmit said electric impulse or to receive electromyographic impulses; an amplifier electrically communicating with said at least one pair of electrodes, said amplifier adapted to amplify said received electromyographic impulses; a filtering unit electrically communicating with said amplifier, said filtering unit being adapted to remove artifacts from the received electromyographic impulses; a commutation block electrically communicating with said at least one pair of electrodes, said commutation block being adapted to alternately transfer the received electromyographic impulses to said amplifier or to transfer the generated electric impulse from said stimulator; a display for displaying said received electromyographic impulses and a predetermined threshold value; and a control unit adapted to receive the electromyographic impulses from said amplifier and to activate said stimulator in a predetermined manner;
    adhering said a least one pair of electrodes to the rehabilitated muscles;

providing a reference electrode;

adhering said reference electrode to the patient in a location relatively remote from the rehabilitated muscles;

connecting said reference electrode to said amplifier; and transmitting said electric impulse to the muscles through said at least one pair of electrodes.

15. The method as claimed in claim 14, the method further comprises receiving electromyographic impulses; feeding said predetermined threshold value; comparing said electromyographic impulses to said predetermined threshold value; transmitting an electric impulse having higher amplitude than the amplitude of the received electromyographic impulse having the highest value to the muscles after said electromyographic impulse exceeds said predetermined threshold value.

16. The method as claimed in claim 15, the method further comprises displaying the transmitted electric impulse on said display and displaying said predetermined threshold value.

* * * * *